US010426933B2

(12) United States Patent
Lee et al.

(10) Patent No.: US 10,426,933 B2
(45) Date of Patent: Oct. 1, 2019

(54) CATHETER HAVING MONOLITHIC MULTILAYER DISTAL OUTER MEMBER

(71) Applicant: ABBOTT CARDIOVASCULAR SYSTEMS INC., Santa Clara, CA (US)

(72) Inventors: Jeong S. Lee, Diamond Bar, CA (US); Kenneth L. Wantink, Temecula, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 171 days.

(21) Appl. No.: 14/843,074

(22) Filed: Sep. 2, 2015

(65) Prior Publication Data
US 2016/0339211 A1 Nov. 24, 2016

Related U.S. Application Data

(60) Provisional application No. 62/163,822, filed on May 19, 2015.

(51) Int. Cl.
*A61M 25/10* (2013.01)
*A61M 25/00* (2006.01)
*A61M 25/01* (2006.01)

(52) U.S. Cl.
CPC ........ *A61M 25/10* (2013.01); *A61M 25/0009* (2013.01); *A61M 25/0045* (2013.01);
(Continued)

(58) Field of Classification Search
CPC ...... A61M 25/0045; A61M 2025/0046; A61M 2025/0047; A61M 2025/0183
See application file for complete search history.

(56) References Cited

U.S. PATENT DOCUMENTS

| | | | |
|---|---|---|---|
| 4,522,867 | A | 6/1985 | Hill, Jr. et al. |
| 4,782,834 | A | 11/1988 | Maguire et al. |

(Continued)

FOREIGN PATENT DOCUMENTS

| | | |
|---|---|---|
| EP | 1 084 728 A1 | 3/2001 |
| EP | 1 306 062 A1 | 5/2003 |

(Continued)

OTHER PUBLICATIONS

U.S. Appl. No. 13/481,441 (U.S. Pat. No. 8,834,510), filed May 25, 2012 (Sep. 16, 2014).

(Continued)

*Primary Examiner* — Nathan R Price
*Assistant Examiner* — Courtney B Fredrickson
(74) *Attorney, Agent, or Firm* — Baker Botts L.L.P.

(57) ABSTRACT

Balloon catheter includes an outer shaft including a hypotube and a monolithic multilayer distal outer member and having an inflation lumen defined therethrough, a balloon in fluid communication with the inflation lumen, and an inner tubular member having a guidewire lumen defined therethrough. The monolithic multilayer distal outer member has a proximal end portion and a distal end portion. The monolithic multilayer distal outer member has an inner layer comprising a first polymer having a tensile strength greater than about 8,000 psi and an outer layer comprising a second polymer having a flexural modulus of less than about 130,000 psi at room temperature. A proximal end of the monolithic multilayer distal outer member is coupled to the hypotube. The monolithic multilayer distal outer member is necked to a reduced diameter along at least a portion of a length thereof. The balloon has a proximal balloon shaft coupled to a distal end of the monolithic multilayer distal outer member. The inner tubular member extends distally from a proximal port in the proximal end portion of the (Continued)

monolithic multilayer distal outer member through at least a portion of the balloon.

23 Claims, 2 Drawing Sheets

(52) U.S. Cl.
CPC . *A61M 25/1029* (2013.01); *A61M 2025/0046* (2013.01); *A61M 2025/0183* (2013.01)

(56) References Cited

U.S. PATENT DOCUMENTS

| | | | |
|---|---|---|---|
| 4,976,690 A | 12/1990 | Solar et al. | |
| 5,156,594 A | 10/1992 | Keith | |
| 5,217,434 A | 6/1993 | Arney | |
| 5,217,482 A | 6/1993 | Keith | |
| 5,279,562 A | 1/1994 | Sirhan et al. | |
| 5,370,616 A | 12/1994 | Keith et al. | |
| 5,370,655 A | 12/1994 | Burns | |
| 5,387,193 A | 2/1995 | Miraki | |
| 5,387,225 A | 2/1995 | Euteneuer et al. | |
| 5,395,334 A | 3/1995 | Keith et al. | |
| 5,423,754 A | 6/1995 | Cornelius et al. | |
| 5,458,615 A | 10/1995 | Klemm et al. | |
| 5,490,837 A | 2/1996 | Blaeser et al. | |
| 5,507,768 A | 4/1996 | Lau et al. | |
| 5,533,968 A | 7/1996 | Muni et al. | |
| 5,643,209 A | 7/1997 | Fugoso et al. | |
| 5,649,909 A | 7/1997 | Cornelius | |
| 5,743,875 A | 4/1998 | Sirhan et al. | |
| 5,833,706 A | 11/1998 | St. Germain et al. | |
| 5,908,406 A | 6/1999 | Ostapchenko et al. | |
| 6,083,232 A | 7/2000 | Cox | |
| 6,102,890 A | 8/2000 | Stivland et al. | |
| 6,217,547 B1 * | 4/2001 | Lee | A61L 29/049 |
| | | | 604/103 |
| 6,277,093 B1 | 8/2001 | Lee | |
| 6,575,958 B1 | 6/2003 | Happ et al. | |
| 6,595,958 B1 | 7/2003 | Mickley | |
| 6,620,127 B2 | 9/2003 | Lee et al. | |
| 6,695,812 B2 | 2/2004 | Estrada et al. | |
| 6,702,802 B1 | 3/2004 | Hancock et al. | |
| 6,746,423 B1 | 6/2004 | Wantink | |
| 6,863,678 B2 * | 3/2005 | Lee | A61L 29/085 |
| | | | 606/192 |
| 6,923,822 B2 | 8/2005 | Crawford et al. | |
| 6,964,750 B2 | 11/2005 | Fulford | |
| 7,001,420 B2 | 2/2006 | Speck et al. | |
| 7,074,206 B2 | 7/2006 | Lee et al. | |
| 7,195,611 B1 | 3/2007 | Simpson et al. | |
| 7,303,798 B2 | 12/2007 | Bavaro et al. | |
| 7,322,959 B2 | 1/2008 | Warnack et al. | |
| 7,549,975 B2 | 6/2009 | Lee et al. | |
| 7,828,766 B2 | 11/2010 | Durcan | |
| 7,833,597 B2 | 11/2010 | Bavaro et al. | |
| 7,862,541 B2 | 1/2011 | Jeffrey et al. | |
| 7,906,066 B2 | 3/2011 | Wilson et al. | |
| 7,951,259 B2 | 5/2011 | Duchamp et al. | |
| 7,967,781 B2 | 6/2011 | Simpson et al. | |
| 7,967,836 B2 | 6/2011 | Warnack et al. | |
| 8,048,058 B2 | 11/2011 | Fulford | |
| 8,052,638 B2 | 11/2011 | Lee et al. | |
| 8,057,430 B2 | 11/2011 | Grovender et al. | |
| 8,251,949 B2 | 8/2012 | Warnack | |
| 8,382,738 B2 * | 2/2013 | Simpson | B29C 66/73713 |
| | | | 604/103.04 |
| 8,394,055 B2 | 3/2013 | Durcan | |
| 8,444,608 B2 | 5/2013 | Haslinger et al. | |
| 8,444,802 B2 | 5/2013 | Lee et al. | |
| 8,637,132 B2 | 1/2014 | Bavaro et al. | |
| 8,834,510 B2 | 9/2014 | Wilson et al. | |
| 8,840,743 B2 | 9/2014 | Wantink et al. | |
| 9,132,259 B2 | 9/2015 | Lin et al. | |
| 2002/0072705 A1 | 6/2002 | Vrba et al. | |
| 2002/0146557 A1 | 10/2002 | Claude et al. | |
| 2003/0125709 A1 | 7/2003 | Eidenschink | |
| 2003/0135231 A1 | 7/2003 | Goodin et al. | |
| 2004/0082935 A1 | 4/2004 | Lee et al. | |
| 2004/0256049 A1 * | 12/2004 | O'Shaughnessy | |
| | | | A61M 25/0009 |
| | | | 156/157 |
| 2005/0070847 A1 | 3/2005 | Van Erp et al. | |
| 2005/0261725 A1 | 11/2005 | Crawford et al. | |
| 2006/0135909 A1 | 6/2006 | Holman et al. | |
| 2007/0021772 A1 | 1/2007 | Von Oepen et al. | |
| 2007/0173919 A1 | 7/2007 | Maschke | |
| 2008/0015499 A1 | 1/2008 | Warnack | |
| 2008/0077085 A1 | 3/2008 | Eidenschink et al. | |
| 2008/0125707 A1 | 5/2008 | Wilson et al. | |
| 2009/0036829 A1 | 2/2009 | Pagel et al. | |
| 2009/0171281 A1 | 7/2009 | Pipenhagen et al. | |
| 2009/0223624 A1 | 9/2009 | Lee et al. | |
| 2010/0130925 A1 | 5/2010 | Haslinger et al. | |
| 2010/0189876 A1 | 7/2010 | Kokish et al. | |
| 2010/0217234 A1 | 8/2010 | Grovender | |
| 2010/0285085 A1 | 11/2010 | Stankus et al. | |
| 2011/0022150 A1 | 1/2011 | Durcan | |
| 2011/0060276 A1 | 3/2011 | Schaeffer et al. | |
| 2011/0070355 A1 | 3/2011 | Bavaro et al. | |
| 2011/0160834 A1 | 6/2011 | Aggerholm | |
| 2011/0172696 A1 | 7/2011 | Jeffrey et al. | |
| 2012/0065718 A1 | 3/2012 | Simpson et al. | |
| 2012/0226229 A1 | 9/2012 | Watanabe et al. | |
| 2012/0302952 A1 | 11/2012 | Kitada et al. | |
| 2012/0302994 A1 | 11/2012 | Wilson et al. | |
| 2012/0303054 A1 | 11/2012 | Wilson et al. | |
| 2013/0178795 A1 | 7/2013 | Wilson et al. | |
| 2014/0276401 A1 | 9/2014 | Lee et al. | |

FOREIGN PATENT DOCUMENTS

| | | |
|---|---|---|
| JP | 6-114109 A | 4/1994 |
| JP | 2001-333984 A | 12/2001 |
| JP | 2008-237844 A | 10/2008 |
| WO | WO 01/43944 A1 | 6/2001 |
| WO | WO 03/037418 A2 | 5/2003 |
| WO | WO 2008/005706 A2 | 1/2008 |
| WO | WO 2012/162651 A1 | 11/2012 |

OTHER PUBLICATIONS

U.S. Appl. No. 14/458,327 (US 2014/0358074), filed Aug. 13, 2014 (Dec. 4, 2014).
U.S. Appl. No. 14/843,249 (US 2016/0067458), filed Sep. 2, 2015 (Mar. 10, 2016).
U.S. Appl. No. 14/843,308 (US 2016/0339204), filed Sep. 2, 2015 (Nov. 24, 2016).
U.S. Appl. No. 14/843,372 (US 2016/0067459), filed Sep. 2, 2015 (Mar. 10, 2016).
U.S. Appl. No. 13/481,441, Aug. 13, 2014 Issue Fee payment.
U.S. Appl. No. 13/481,441, Jun. 18, 2014 Notice of Allowance.
U.S. Appl. No. 13/481,441, Apr. 18, 2014 Response to Non-Final Office Action.
U.S. Appl. No. 13/481,441, Dec. 18, 2013 Non-Final Office Action.
U.S. Appl. No. 13/481,441, Sep. 12, 2013 Response to Restriction Requirement.
U.S. Appl. No. 13/481,441, Aug. 15, 2013 Restriction Requirement.
U.S. Appl. No. 14/458,327, Dec. 5, 2016 Notice of Allowance.
U.S. Appl. No. 14/458,327, Nov. 14, 2016 Response to Restriction Requirement.
U.S. Appl. No. 14/458,327, Sep. 13, 2016 Restriction Requirement Filed.
European Search Report dated Jan. 29, 2016 in EP Application No. 15183531.
European Search Report dated Oct. 13, 2016 in Application No. EP 15183533.
European Search Report dated Oct. 14, 2016 in Application No. EP 15183534.
International Search Report for PCT/US2012/039678, dated Sep. 21, 2012 (Corresponds to U.S. Appl. No. 13/481,441).

(56) References Cited

OTHER PUBLICATIONS

Partial European Search Report dated Jan. 29, 2016 in EP Application No. 15183539.
U.S. Appl. No. 14/458,327, Mar. 3, 2017 Issue Fee Payment.
U.S. Appl. No. 14/843,308, Apr. 4, 2017 Non-Final Office Action.
U.S. Appl. No. 14/843,372, Apr. 4, 2017 Non-Final Office Action.
U.S. Appl. No. 15/449,462 (US 2017/0173308), filed Mar. 3, 2017 (Jun. 22, 2017).
U.S. Appl. No. 14/843,249, Jul. 12, 2017 Non-Final Office Action.
U.S. Appl. No. 14/843,308, Aug. 4, 2017 Response to Non-Final Office Action.
U.S. Appl. No. 14/843,372, Aug. 4, 2017 Response to Non-Final Office Action.
U.S. Appl. No. 14/843,249, May 18, 2018 Applicant Initiated Interview Summary.
U.S. Appl. No. 14/843,249, May 8, 2018 Response after Final Action.
U.S. Appl. No. 14/843,308, May 17, 2018 Amendment and Request for Continued Examination (RCE).
U.S. Appl. No. 14/843,308, May 15, 2018 Applicant Initiated Interview Summary.
U.S. Appl. No. 14/843,308, May 1, 2018 Advisory Action.
U.S. Appl. No. 14/843,308, Apr. 12, 2018 Response after Final Action.
U.S. Appl. No. 14/843,372, May 16, 2018 Applicant Initiated Interview Summary.
U.S. Appl. No. 14/843,249, Nov. 21, 2017 Final Office Action.
U.S. Appl. No. 14/843,249, Oct. 12, 2017 Response to Non-Final Office Action.
U.S. Appl. No. 14/843,308, Nov. 17, 2017 Final Office Action.
U.S. Appl. No. 14/843,372, Nov. 21, 2017 Final Office Action.

* cited by examiner

CATHETER HAVING MONOLITHIC MULTILAYER DISTAL OUTER MEMBER

REFERENCE TO RELATED APPLICATIONS

This application claims priority to U.S. Provisional Patent Application No. 62/163,822, filed on May 19, 2015, the contents of which is hereby incorporated by reference in its entirety.

BACKGROUND

Field

The presently disclosed subject matter relates to devices for use in percutaneous transluminal coronary angioplasty (PTCA) or stent delivery systems or the like. Particularly, the disclosed subject matter is related to a catheter having a monolithic multilayer distal outer member.

Description of Related Art

In percutaneous transluminal coronary angioplasty (PTCA) procedures, a guiding catheter is advanced in the vasculature of a patient until the distal tip of the guiding catheter is seated in a desired coronary artery. A guidewire is advanced out of the distal end of the guiding catheter into the coronary artery until the distal end of the guidewire crosses a lesion to be dilated. A dilatation catheter, having an inflatable balloon on the distal portion thereof, is advanced into the coronary anatomy over the previously introduced guidewire until the balloon of the dilatation catheter is positioned across the lesion. Once positioned, the dilatation balloon is inflated with inflation fluid one or more times to a predetermined size at a suitable pressure to compress the stenosis against the arterial wall to open up the vascular passageway. Generally, the inflated diameter of the balloon is approximately the same diameter as the native diameter of the body lumen being dilated to complete the dilatation but not over expand the artery wall. After the balloon is deflated, blood resumes flowing through the dilated artery and the dilatation catheter and the guidewire can be removed therefrom.

In such angioplasty procedures, there may be restenosis of the artery, i.e., reformation of the arterial blockage, which necessitates either another angioplasty procedure, or some other method of repairing or strengthening the dilated area. To reduce the restenosis rate and to strengthen the dilated area, physicians may additionally or alternatively implant an intravascular prosthesis inside the artery at the site of the lesion. Such stents or scaffolds may be bare metal, polymeric, or coated with a drug or other therapeutic agent. Stents or scaffolds may also be used to repair vessels having an intimal flap or dissection or to generally strengthen a weakened section of a vessel. Stents or scaffolds are usually delivered to a desired location within a coronary artery in a contracted condition on a balloon of a catheter which is similar in many respects to a balloon angioplasty catheter and expanded to a larger diameter by expansion of the balloon. The balloon is deflated to remove the catheter with the stent implanted within the artery at the site of the dilated lesion. Coverings on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON® may be implanted in vessels to strengthen or repair the vessel, or used in an anastomosis procedure to connect vessels segments together. For details of example stents, see for example, U.S. Pat. No. 5,507,768 to Lau, et al. and U.S. Pat. No. 5,458,615 to Klemm, et al., the contents of each of which are incorporated herein by reference in their entireties.

In addition to percutaneous transluminal angioplasty (PTA), PTCA, and atherectomy procedures, balloon catheters are also used to treat the peripheral system such as in the veins system or the like. For instance, a balloon catheter is initially advanced over a guidewire to position the balloon adjacent a stenotic lesion. Once in place, the balloon is then inflated, and the restriction of the vessel is opened, and a stein or scaffold can be delivered if desired. Likewise, balloon catheters are also used for treatment of other luminal systems throughout the body.

Typically, balloon catheters comprise a hollow catheter shaft with a balloon secured at a distal end. The interior of the balloon is in a fluid flow relation with an inflation lumen extending along a length of the shaft. Fluid under pressure can thereby be supplied to the interior of the balloon through the inflation lumen. To position the balloon at the stenosed region, the catheter shaft is designed in multiple parts to have suitable pushability (i.e., the ability to transmit force along the length of the catheter), trackability, and flexibility, to be readily advanceable within the tortuous anatomy of the vasculature. The catheter is also designed so that it can be withdrawn from the patient after delivery. Conventional balloon catheters for intravascular procedures, such as angioplasty and stent delivery, frequently have a relatively stiff proximal shaft section to facilitate advancement of the catheter within the body lumen, a mid-shaft section of an intermediate (or transition) flexibility, and a relatively flexible distal shaft section to facilitate passage through tortuous anatomy, such as distal coronary and neurological arteries, without damage to the vessel wall or damage to the stent, in the case of stent delivery.

Traditional catheter shafts are often constructed with inner and outer member tubing with an annular space therebetween for balloon inflation. In the design of catheter shafts, it is desirable to predetermine or control characteristics such as strength, stiffness and flexibility of various sections of the catheter shaft to provide desired catheter performance. This is conventionally performed by combining separate lengths of tubular members of different material and/or dimensions and then assembling the separate members into a single shaft length. However, the transition between sections of different stiffness or material can be a cause of undesirable kinking along the length of the catheter. Such kinking is particularly evident in rapid exchange (RX) catheters, wherein the proximal shaft section does not include the additional structure of a guidewire lumen tube. For example, a conventional RX catheter generally consists of a proximal hypotube having a single inflation lumen therethrough, a mid-shaft transition section, and a dual lumen or coaxial tube configuration at a distal end section having both a guidewire lumen and an inflation lumen therein. Known techniques to minimize kinking at the transition between the more rigid proximal section and the more flexible distal section include bonding two or more segments of materials having different flexibility together to form the shaft. Such transition bonds need to be sufficiently strong to withstand the pulling and pushing forces on the shaft during use.

To address the described issues, catheters having varied flexibility and/or stiffness have been developed with various sections of the catheter shaft that are specifically tailored to provide desired catheter performance. For example, each of U.S. Pat. No. 4,782,834 to Maguire and U.S. Pat. No.

5,370,655 to Burns discloses a catheter having sections along its length which are formed from materials having a different stiffness; U.S. Pat. No. 4,976,690 to Solar discloses a catheter having an intermediate waist portion which provides increased flexibility along the catheter shaft; U.S. Pat. No. 5,423,754 to Cornelius discloses a catheter having a greater flexibility at its distal portion due to both a material and dimensional transition in the shaft; U.S. Pat. No. 5,649,909 to Cornelius discloses a catheter having a proximal portion with greater stiffness due to the application of a polymeric coating thereto; and U.S. Pat. No. 8,444,608 to Haslinger discloses a multilayer catheter shaft using a combination of a high Shore D durometer value material and a lower Shore D durometer value material to reduce kinking, the contents of each of which are incorporated herein by reference in their entireties.

However, one difficulty has been balancing the often competing characteristics of strength and flexibility of the catheter shaft. In addition, use of multiple shaft sections can be a cause of undesirable kinking along the length of the catheter, and the bonds between the sections can be a location of failure (e.g. rupture) if any defects in the bonds exist.

As such, there remains a need for a catheter having a shaft with an improved combination of characteristics such as strength, flexibility, ease of manufacture, and lower cost. There is also a need for a catheter that has improved trackability to facilitate further passage through tortuous anatomy, such as distal coronary arteries, while maintaining the ability to withdraw from the tortuous anatomy without failure. There is also a need for a catheter having an outer member which is capable of being bonded to both a proximal metal hypotube and an inflatable balloon.

SUMMARY

The purpose and advantages of the disclosed subject matter will be set forth in and are apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter provides a balloon catheter including an outer shaft including a hypotube and a monolithic multilayer distal outer member and having an inflation lumen defined therethrough, a balloon in fluid communication with the inflation lumen, and an inner tubular member having a guidewire lumen defined therethrough. The monolithic multilayer distal outer member has a proximal end portion and a distal end portion. The monolithic multilayer distal outer member has an inner layer comprising a first polymer having a tensile strength greater than about 8,000 psi and an outer layer comprising a second polymer having a flexural modulus of less than about 130,000 psi at room temperature. A proximal end of the monolithic multilayer distal outer member is coupled to the hypotube. The monolithic multilayer distal outer member is necked to a reduced diameter along at least a portion of a length thereof. The balloon has a proximal balloon shaft coupled to a distal end of the monolithic multilayer distal outer member. The inner tubular member extends distally from a proximal port in the proximal end portion of the monolithic multilayer distal outer member through at least a portion of the balloon.

As embodied herein the second polymer can be polyether block amide (for example commercially available as Pebax®). The polyether block amide can have a Shore D hardness between 63D and 72D. In some embodiments the first polymer can be nylon. The nylon can be selected from the group consisting of nylon 12, nylon 11, and copolymers thereof.

Additionally, and as embodied herein, the monolithic multilayer distal outer member can have at least one intermediate layer disposed between the inner layer and the outer layer. The balloon catheter can include an inner tubular member coupled to the monolithic multilayer distal outer member at the proximal port. The inner tubular member can include a multilayer inner tubular member. The multilayer inner tubular member can include an inner lubricious layer and an outer layer of polyether block amide, such as Pebax®.

In some embodiments, the monolithic multilayer distal outer member is necked to the reduced diameter along a portion of the length thereof such that the proximal end portion has a proximate outer diameter and the distal end portion has a distal outer diameter, the proximal outer diameter being greater than the distal outer diameter. Alternatively, the monolithic multilayer distal outer member is necked to the reduced diameter along an entire length thereof such that the monolithic multilayer distal outer member has a constant diameter along the entire length thereof.

In some embodiments, the monolithic multilayer distal outer member is necked to the reduced diameter along a first portion of the length thereof and necked to a second reduced diameter along a second portion of the length thereof such that the proximal end portion has a proximate outer diameter and the distal end portion has a distal outer diameter, the proximal outer diameter being greater than the distal outer diameter. Additionally, the monolithic multilayer distal outer member can be necked to a third reduced diameter along a third portion of the length thereof, the third portion can be proximate the proximal balloon shaft.

As embodied herein, the hypotube can further comprise a distal end, and an outer surface of the hypotube can be roughened proximate the distal end.

The disclosed subject matter also provides a balloon catheter having an outer shaft including a hypotube and a monolithic multilayer distal outer member. The outer shaft has an inflation lumen defined therethrough. The monolithic multilayer distal outer member has a proximal end portion and a distal end portion. The monolithic multilayer distal outer member has an inner layer comprising a first polymer having a tensile strength greater than about 8,000 psi and an outer layer comprising a second polymer having a flexural modulus of less than about 130,000 psi at room temperature. A proximal end of the monolithic multilayer distal outer member is coupled to the hypotube. The monolithic multilayer distal outer member is necked to a reduced diameter along at least a portion of a length thereof such that the proximal end portion has a proximate outer diameter and the distal end portion has a distal outer diameter. The proximal outer diameter is greater than the distal outer diameter. The balloon catheter also includes a balloon in fluid communication with the inflation lumen. The balloon has a proximal balloon shaft coupled to a distal end of the monolithic multilayer distal outer member. The balloon catheter also includes an inner tubular member having a guidewire lumen defined therethrough. The inner tubular member extends distally from a proximal port in the proximal end portion of the monolithic multilayer distal outer member through at least a portion of the balloon. This balloon catheter can include any or all of the features described for the balloon catheter herein above.

The disclosed subject matter also provides a method of making a balloon catheter. The method includes necking a tubular member to form a monolithic multilayer distal outer member necked along at least a portion of a length thereof. The monolithic multilayer distal outer member has an inner layer comprising a first polymer having a tensile strength greater than about 8,000 psi and an outer layer comprising a second polymer having a flexural modulus of less than about 130,000 psi at room temperature. The method also includes providing a hypotube, coupling a proximal end of the monolithic multilayer distal outer member to the hypotube to form an outer shaft having an inflation lumen defined therethrough, providing a balloon in fluid communication with the inflation lumen, the balloon having a proximal balloon shaft, coupling the proximal balloon shaft to a distal end of the monolithic multilayer distal outer member, and providing an inner tubular member having a guidewire lumen defined therethrough. The inner tubular member extends distally from a proximal port in the monolithic multilayer distal outer member through at least a portion of the balloon. This method can include any or all of the features described for the balloon catheters herein above.

DETAILED DESCRIPTION

Reference will now be made in detail to the various exemplary embodiments of the disclosed subject matter, exemplary embodiments of which are illustrated in the accompanying drawings. The structure and corresponding method of making of the disclosed subject matter will be described in conjunction with the detailed description of the catheter.

In accordance with the disclosed subject matter herein, a balloon catheter is provided including an outer shaft including a hypotube and a monolithic multilayer distal outer member and having an inflation lumen defined therethrough, a balloon in fluid communication with the inflation lumen, and an inner tubular member having a guidewire lumen defined therethrough. The monolithic multilayer distal outer member has a proximal end portion and a distal end portion. The monolithic multilayer distal outer member has an inner layer comprising a first polymer having a tensile strength greater than about 8,000 psi and an outer layer comprising a second polymer having a flexural modulus of less than about 130,000 psi at room temperature. A proximal end of the monolithic multilayer distal outer member is coupled to the hypotube. The monolithic multilayer distal outer member is necked to a reduced diameter along at least a portion of a length thereof. The balloon has a proximal balloon shaft coupled to a distal end of the monolithic multilayer distal outer member. The inner tubular member extends distally from a proximal port in the proximal end portion of the monolithic multilayer distal outer member through at least a portion of the balloon.

Figure 1:
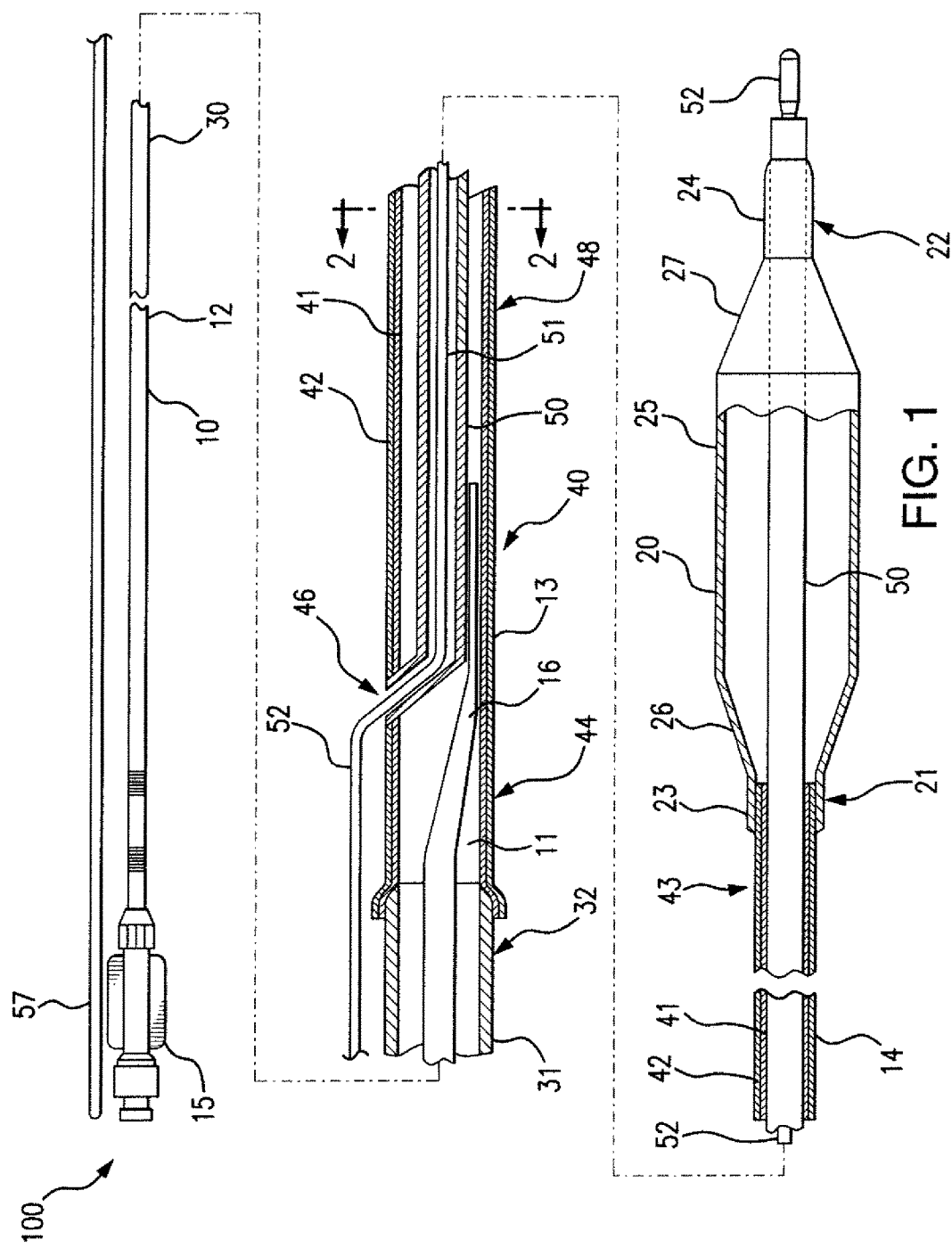
FIG. 1 schematically depicts a representative embodiment of a catheter in accordance with certain aspects of the disclosed subject matter.
Figure 2:
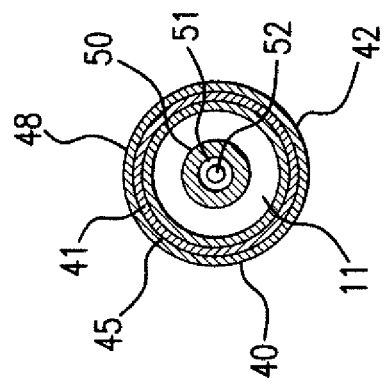
FIG. 2 is a transverse cross-sectional view of an embodiment of the catheter shaft along line 7-7.
Figure 3:
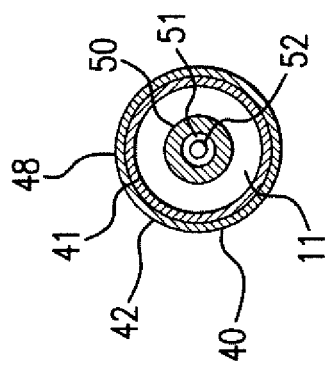
FIG. 3 is a transverse cross-sectional view of an alternative embodiment of the catheter shaft along line 7-7.

The accompanying figures, where like reference numerals refer to identical or functionally similar elements, throughout the separate views, serve to further illustrate the various embodiments and to explain various principles and advantages all in accordance with the disclosed subject matter. For the purpose of explanation and illustration, and not limitation, an exemplary embodiment of an balloon catheter having a monolithic multilayer distal outer member is shown in FIGS. 1-3. The catheters having a monolithic multilayer distal outer member described herein, and methods of making and using the catheters, are not limited to the illustrative embodiments described or depicted herein.

For the purpose of illustration and not limitation, FIGS. 1-3 illustrate an embodiment of the disclosed subject matter, a balloon catheter 100, which is a rapid exchange catheter. As illustrated in FIG. 1, catheter 100 includes an elongated catheter shaft 10 having a proximal end, a distal end, an outer shaft 13, a proximal shaft section 12, a distal shaft section 14. The outer shaft has an inflation lumen 11 defined therethrough. The proximal shaft section 12 can be a hypotube 30 having a distal end 31 and an outer surface 32. The hypotube 30 can be made of any suitable material, for example a metal such as stainless steel. In some embodiments, the hypotube 30 can be roughened proximate the distal end 31 to allow for improved bonding to a monolithic multilayer distal outer member 40. The elongated catheter shaft 10 also includes an inner tubular member 50. The monolithic multilayer distal outer member 40 has a tubular wall 48 with an inner layer 41 and an outer layer 42. The monolithic multilayer distal outer member 40 also includes a distal end portion 43 and a proximal end portion 44. Inflation lumen 11 is defined by the multilayered tubular member 40. The inner tubular member 50 has a guidewire lumen 51 defined therein that can be adapted to slidingly receive a guidewire 52. The catheter 100 can also include an inflatable balloon 20, disposed on the distal end portion 43 of the monolithic multilayer distal outer member 40. The balloon 20 can have a proximal end 21 and a distal end 22.

The inner layer 41 of the monolithic multilayer distal outer member 40 can comprise a first polymer having a tensile strength greater than about 8,000 psi. For example, and not limitation, the inner layer 41 can comprise nylon, for example, nylon 12, nylon 11, or copolymers thereof. The outer layer 42 of the monolithic multilayer distal outer member 40 can comprise a second polymer having a flexural modulus of less than about 130,000 psi at room temperature. For example, and not limitation, the outer layer 42 can comprise polyether block amide (for example commercially available as Pebax®). The polyether block amide can have a Shore D hardness between 63D and 72D, and can be, for example, Pebax® 63D, Pebax® 70D, or Pebax® 72D. The monolithic multilayer distal outer member 40 can be formed by coextruding a tubular product formed from the two polymeric components to create a tubular member having an outer layer 42 and an inner layer 41 of the two polymeric materials using a coextruder, as known to one of ordinary skill in the art.

As shown in FIG. 1, for the purpose of illustration and not limitation, a proximal port 46 can be provided in a tubular wall 48 of the proximal end portion 44 of the monolithic multilayer distal outer member 40 and can be in fluid communication with the lumen 51 of the inner tubular member 50. The inner tubular member 50 can be coupled to the monolithic multilayer distal outer member 40 at the proximal port 46. The guidewire 52 can exit the catheter proximally from the proximal port 46 and extend alongside and exteriorly of the proximal section 12 to the proximal end of the catheter 100.

Figure 4:
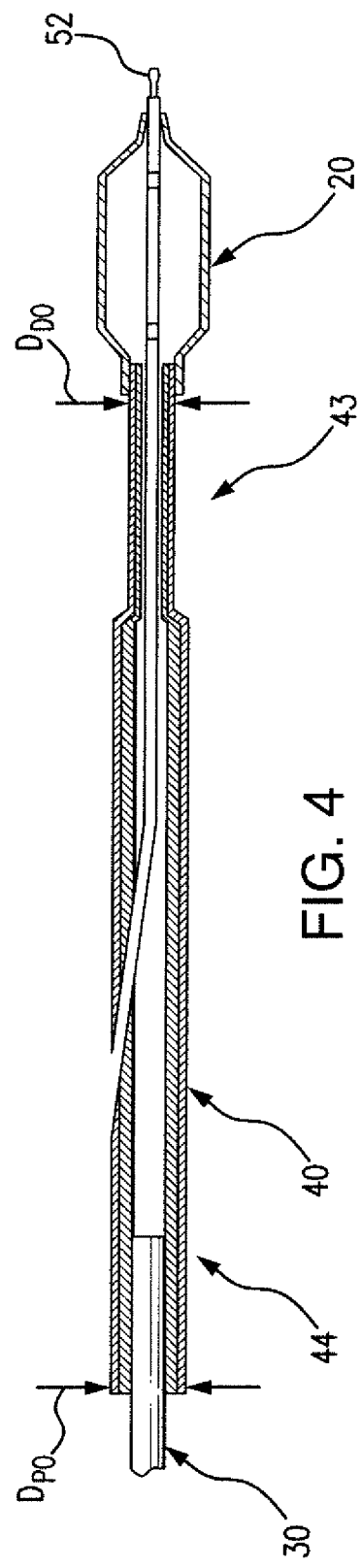
FIG. 4 schematically depicts a partial representative embodiment of a catheter in accordance with certain aspects of the disclosed subject matter.

The monolithic multilayer distal outer member 40 can be necked to a reduced diameter along at least a portion of a length thereof. For example, as shown in FIG. 4 for the purpose of illustration, the monolithic multilayer distal outer member can necked to the reduced diameter along a portion of the length thereof such that the proximal end portion 44 of the monolithic multilayer distal outer member 40 can have a proximal outer diameter $D_{PO}$ and the distal end portion 43 of the monolithic multilayer distal outer member 40 can have a distal outer diameter $D_{DO}$. As further illustrated in FIG. 4, the distal outer diameter $D_m$ can be less than the proximal outer diameter $D_{PO}$. In some embodiments, the monolithic multilayer distal outer member is necked to a reduced diameter $D_{PO}$ along a first portion of the length thereof and necked to a second reduced diameter $D_{DO}$ along a second portion of the length thereof such that the proximal end portion has a proximate outer diameter and the distal end portion having a distal outer diameter, the proximal outer diameter being greater than the distal outer diameter. Additionally, the monolithic multilayer distal outer member can be necked to a third reduced diameter $D_3$ along a third portion of the length thereof (not shown). The third reduced diameter can be smaller than the rest of the distal outer member 40 and can be proximate the proximal balloon shaft 23 to allow the proximal balloon shaft 23 to more easily fit over the distal outer member 40 for heat bonding to a reduce profile.

Alternatively, the monolithic multilayer distal outer member can be necked to the reduced diameter along an entire length thereof such that the monolithic multilayer distal outer member has a constant diameter along the entire length thereof.

In accordance with the disclosed subject matter, necking the distal outer member 40 can provide for more precise dimensions and decreased tolerances, can impart shear on the material, and can introduce partial orientation in the polymer material, which can increase the strength of the distal outer member 40 without significantly effecting flexibility and provide for increased stent or scaffold push. Also, introduction of partial (e.g., linear) orientation in the polymer material of the distal outer member 40 can provide more column strength, more push, and can still allow for some play (e.g., stretching or elongating) during withdrawal from the tortuous anatomy and decrease the likelihood of rupture or separation as compared to a shaft made of a fully oriented polymer material (e.g., blown).

At the junction between the hypotube 30 and the monolithic multilayer distal outer member 40, the proximal end portion 44 of the monolithic multilayer distal outer member 40 can be configured to receive at least a portion of the distal end 31 of the hypotube 30. The inner layer 41 of the multilayered tubular member 40 can be coupled to the outer surface 32 of the hypotube 30 Multilayer distal outer member 40 allows for selection of the material of inner layer 41 to be bond compatible with hypotube 30. For example, in some embodiments, the metal hypotube 30 will be coupled to the nylon inner layer 41 of the monolithic multilayer distal outer member 40. The hypotube 30 and monolithic multilayer distal outer member 40 can be couple by any known means, for example by applying heat to the area of overlap. For example and without limitation, electromagnetic energy, such as thermal, laser, or sonic energy, can be applied to the distal outer member 40 to bond to hypotube 30.

At the junction between the balloon 20 and the monolithic multilayer distal outer member 40, the proximal end 21 and proximal balloon shaft 23 of the balloon 20 can be sealingly secured to the outer layer 42 of the monolithic multilayer distal outer member 40, proximate the distal end portion 43 of the monolithic multilayer distal outer member 40. Multilayer distal outer member 40 allows for selection of the material of outer layer 42 to be bond compatible with the material of balloon 20 (which can be a different material than inner layer 41, which can be bond compatible with hypotube 30.

The interior of the balloon 20 can be in fluid communication with the inflation lumen 11. For example, in some embodiments, the inflatable balloon 20 can be coupled to the outer surface 42 of the monolithic multilayer distal outer member 40. The inflatable balloon 20 can have a proximal balloon shaft 23 at the junction between the balloon 20 and the tubular member 40. The balloon 20 can further include a distal balloon shaft 24 sealingly secured to the distal end of the inner tubular member 50. The balloon can also include a working length 25 between the proximal cone section 26 and the distal cone section 27. An adaptor 15 at the proximal end of the shaft can be configured to direct inflation fluid into inflation lumen 11 and balloon so.

The proximal balloon shaft 23 of the balloon 20 can be fusion boned to the outer layer 42 of the monolithic multilayer distal outer member 40, for example, by applying heat to the area of overlap. For example and without limitation, electromagnetic energy, such as thermal, laser, or sonic energy, can be applied to the proximal balloon shaft 23 of the balloon 20 to bond at least a portion of the proximal balloon shaft 23 to outer layer 42. Heating the proximal balloon shaft of the balloon causes the polymeric material of the balloon 20 to soften, or melt and flow. In some embodiments, a heat shrink tubing (not shown) can be positioned around the outside of the proximal balloon shaft 23 of the balloon 20. The heat shrink tubing, also referred to as a "heat shrink sleeve," can be composed of a polymeric material configured to shrink when exposed to heat. U.S. Pat. No. 7,951, 259, which is hereby incorporated by reference in its entirety, discloses the use of a heat shrink sleeve in fabricating a catheter with a flexible distal end. The heat shrink tubing, when heated, shrinks and exerts an inward radial force on the proximal balloon shaft 23. With the polymer of the proximal balloon shaft 23 in a molten or softened state, the diameter of the proximal sleeve will be reduced by the force exerted by the heat shrink tubing. After the balloon is cooled, the heat shrink tubing can be removed. Heating can be accomplished, for example, by laser heating (e.g., using a $CO_2$ laser), contact heating (e.g., using aluminum nitride, resistance, RF), hot air, resistance heating, induction heating or the like. As embodied herein, for purposes of illustration and not limitation, a solid state laser can be used to heat the shrink tubing and soften the proximal balloon shaft 23. As a result, the outer surface of the proximal balloon shaft 23, in its softened or molten state, can bond to the outer surface of the distal end portion 43 of the monolithic multilayer distal outer member 40. The distal balloon shaft 24 of the balloon 20 can be bonded with the distal section of the inner tubular member 50, in the same manner, which can provide a tapered atraumatic distal end region (or tip) of the catheter.

A support mandrel 16 can be disposed in the inflation lumen 11, with a distal end distal to the proximal port 46. The mandrel is typically a metal member, such as a stainless steel or NiTi member, enhancing the pushability of the catheter 100. Alternatively, the distal end 31 of the hypotube 30 can include a skive as known to one of ordinary skill in the art and as described in U.S. Patent Publication No. 2012/0303054, the contents of which are fully incorporated herein by reference.

FIG. 2 shows, for the purpose of illustration and not limitation, an enlarged cross-sectional view of the catheter 100 along line 2-2 in FIG. 1. Starting from the center, and moving outwardly, there is a guidewire 52 disposed within a guidewire lumen 51 defined by the inner tubular member 50. The inner tubular member 50 is disposed within the inflation lumen 11 defined by the monolithic multilayer distal outer member 40. The monolithic multilayer distal outer member 40 includes inner layer 41 and outer layer 42. In some embodiments, a coating, such as a lubricious coating conventionally used on catheter shafts, can optionally be provided on at least a section of the outer surface of the monolithic multilayer distal outer member 40.

As embodied herein, the multilayer distal outer member 40 is a monolithic construction that extends distally from the hypotube 30 to the balloon 20. By contrast, typical balloon catheters include a separate midshaft portion bonded to the hypotube on one end and a separate distal outer shaft on the other end at a mid-lap seal. The monolithic construction of distal outer member 40, in accordance with the disclosed subject matter, thus provides a jointless outer member extending from the hypotube 30 all the way to the proximal balloon shaft 23 and eliminates the mid lap-seal (between typical mid-shaft and distal-shaft sections), which is one potential location of failure in known, balloon catheters. The monolithic construction of distal outer member 40, in accordance with the disclosed subject matter, can provide a simpler design, easier and less expensive manufacturing, and less parts.

In some embodiments, the monolithic multilayer distal outer member 40 can include an intermediate layer 45, as best shown in FIG. 3. Depending upon the material used, the intermediate layer 45 can provide an improved moisture barrier, improved binding to the materials of the outer layer 42 and inner layer 41, and/or reduced delamination during further processing of the catheter shaft (e.g., thermal bonding to other catheter components). In alternative embodiments (not shown) there can be a plurality of middle layers.

For example, the middle layer 45 can be a tie layer and can improve the binding of non-compatible or less-compatible first and second polymers and reduce delamination thereof during further processing of the catheter shaft including but not limited to thermal bonding to other catheter components (e.g., balloon and/or other shaft section). The intermediate layer can include any suitable tie material known to one of ordinary skill in the art, such as ethylene acrylic acid copolymers, available commercially as Primacor EAA from Dow Chemical, ethylene methacrylic acid copolymers, available commercially as Nucrel from DuPont, and/or Plexar tie layer resin available from LyondellBasell.

In accordance with one aspect, the inner tubular member 50 can comprise a single material of monolithic construction or a multilayered tube. For example, the inner tubular member can be a multilayered tubular member and include at least an inner layer and an outer layer including any of the materials of construction, features, and/or layers as described herein. Additionally or alternatively, the inner tubular member 50 can include a lubricious inner liner and bondable outer layer such as nylon or polyether block amides (for example commercially available as Pebax®), or any of other suitable materials for the intended purpose. In one embodiment, the inner tubular member 50 can include a first inner layer comprising a high density polyethylene (HDPE), a second intermediate layer comprising an adhesive layer, e.g., Primacor, and third outer layer comprising Pebax®. Other examples of suitable materials for inner tubular member 50 are identified in U.S. Pat. Nos. 6,277,093 and 6,217,547, each of which is hereby incorporated by reference in its entirety. The inner tubular member 50 can be formed by conventional methods including but not limited to extrusion or coextrusion.

In accordance with one embodiment of the disclosed subject matter, the balloon 20 can be composed of a wide variety of suitable materials, for example, nylon, co-polyamide such as polyether block amide (for example commercially available as Pebax®), polyester, co-polyester, polyurethane, polyethylene, or the like. Additional suitable materials are provided in U.S. Pat. Nos. 7,074,206, 7,828, 766, and 8,052,638, each of which is hereby incorporated by reference in its entirety. Alternatively or additionally, in some embodiments the balloon 20 can be a multilayer balloon (not shown), for example, as described in U.S. patent application Ser. No. 14/212,966, which is hereby incorporated by reference in its entirety. The balloon 20 can have a first layer made of a first polymer material having a first durometer, and a second layer made of a second polymer having a second durometer. As embodied herein, the second durometer can be greater than the first durometer, and the second layer can be an outer layer relative to the first layer. For example and not limitation, the balloon can have a first layer composed of Pebax® having a durometer of between 55D and about 63D. The second layer can be composed of, for example, Pebax® having a durometer of between about 70D and about 72D.

Balloon 20 can have a noninflated configuration with wings wrapped around the balloon to form a low profile configuration for introduction and advancement within a patient's body lumen. As a result, the balloon inflates to a nominal working diameter by unfolding and filling the molded volume of the balloon. As described above, balloon 20 can have a working length 25, a distal cone section 27, and a distal balloon shaft 23. The distal balloon shaft 23 can have a first segment with a first diameter and a first wall thickness. The distal balloon shaft 23 can have a second segment with a second diameter and a second thickness. The second diameter can be greater than the first diameter and the second wall thickness can be thinner than the first wall thickness as described in U.S. application Ser. No. 13/609, 968, the contents of which is incorporated herein in its entirety.

For the purpose of example and as embodied herein, the balloon 20 can be formed using a technique similar to that disclosed in U.S. Pat. Nos. 6,620,127, 7,828,766, 7,906,066, and 8,052,638, each of which is hereby incorporated by reference in its entirety. In some embodiments, the balloon 20 can be formed by melt-extruding a thermoplastic polymeric material to form a tube, then blow molding or forming in a mold into a blown balloon at a temperature less than an elevated temperature of the melt-extrusion under high pressure, for example between about 150 and about 500 psi. The blow molding can include placing the extruded tube within a mold or capture member. The extruded tube can be radially expanded under suitable conditions by introducing a pressurized fluid into the tube lumen until the outer surface of the extruded tube engages and conforms to the inner surface of the capture member. Furthermore, the polymeric material of the extruded tube can be biaxially oriented by axially expanding the extruded tube with a load applied on at least one end of the tube while radially stretching the extruded tube with a pressurized media in the tube lumen.

In accordance with another aspect, the balloon 20 can be formed using a two stage blow mold process such as disclosed in U.S. Patent Application No. 2012/0065718, which is hereby incorporated by reference in its entirety.

For purpose of illustration and not limitation, and with reference to a coronary balloon catheter, the length of the balloon catheter disclosed herein can generally be about 100 to about 200 centimeters, preferably about 135 to about 150 centimeters, and typically about 145 centimeters for PTCA, and can have other suitable dimensions for other various applications. The monolithic multilayer distal outer member can have, for the purpose of example and not limitation, an outer diameter (OD) of about 0.042 inch (1.07 mm) to about 0.10 inch (2.54 mm), and an inner diameter (ID) of about 0.033 inch (0.84 mm) to about 0.088 inch (2.23 mm). The inner tubular member can have, for purpose of example and not limitation, an OD of about 0.022 inch (0.56 mm) to about 0.050 inch (1.27 mm), and an ID of about 0.015 inch (0.38 mm) to about 0.040 inch (1.00 mm) depending on the diameter of the guidewire to be used with the catheter. For purpose of example and not limitation, the balloon can have a length of about 6 mm to about 100 mm, and an inflated working diameter of about 1.2 mm to about 10 mm.

When a catheter in accordance with the disclosed subject matter is used in an angioplasty procedure, the balloon catheter is advanced over the guidewire until the balloon is properly positioned across the stenosis. The balloon can be inflated in a conventional manner by introducing inflation fluid through the inflation lumen. After one or more inflations, the balloon is deflated and the catheter removed from the patient. A similar procedure is used when the balloon has a stent or scaffold (not shown) mounted thereon for implanting the stent in the body lumen. For example, a radially expandable stent can be releasably mounted on the balloon 20 for delivery and deployment within the body lumen. The balloon catheter can be advanced in the body lumen with the balloon 20 in a noninflated configuration, and the balloon 20 can be inflated by introducing inflation fluid into the balloon interior to expand the balloon 20 and stent mounted thereon. The balloon 20 can then be deflated to allow for repositioning or removal of the catheter from the body lumen, leaving the stent implanted in the body lumen.

To the extent not previously discussed herein, the various catheter components can be formed and joined by conventional materials and methods. For example, one or more section of the tubular member can be a biaxially oriented tubular member and can include a tapered region, as described in detail in U.S. Patent Application No. 2013/0178795, which is incorporated by reference in its entirety. Likewise, inner tubular member can be formed by conventional techniques, such as disclosed in U.S. Pat. Nos. 6,277,093, and 6,217,547, each of which is incorporated by reference in its entirety. Additionally, although not illustrated, coiled or braided reinforcements can be included in the shaft at various locations, as is conventionally known and disclosed in U.S. Pat. No. 7,001,420, which is incorporated by reference in its entirety.

While the present disclosed subject matter has been described herein in terms of certain preferred embodiments, those skilled in the art will recognize that modifications and improvements can be made without departing from the scope of the disclosed subject matter. For example, although the catheters illustrated herein include balloon catheters, the catheter having a monolithic multilayer distal outer member in accordance with the disclosed subject matter can be a variety of suitable catheters, including stent delivery catheters having a retractable sheath or sleeve over a working device (e.g., stent). In such embodiments, the sheath or sleeve can be a monolithic multilayer distal outer member having any of the layers, materials of construction, features, and benefits described herein. While individual features of one embodiment of the disclosed subject matter may be discussed or shown in the drawings of one embodiment and not in other embodiments, it should be apparent that individual features of one embodiment can be combined with one or more features of another embodiment or features from a plurality of embodiments.

The invention claimed is:

1. A balloon catheter, comprising:
an outer shaft including a hypotube and a monolithic multilayer distal outer member of polymer material, the outer shaft having an inflation lumen defined therethrough, the monolithic multilayer distal outer member having a proximal end portion and a distal end portion, the monolithic multilayer distal outer member having an inner layer comprising a first polymer having a tensile strength greater than 8,000 psi and an outer layer comprising a second polymer having a flexural modulus of less than 130,000 psi at room temperature, wherein a proximal end of the monolithic multilayer distal outer member is coupled to the hypotube, wherein the monolithic multilayer distal outer member is necked to a reduced diameter along an entire length thereof with the polymer material consisting essentially of polymer chains in a linear orientation;
a balloon in fluid communication with the inflation lumen, the balloon having a proximal balloon shaft coupled to a distal end of the monolithic multilayer distal outer member; and
an inner tubular member having a guidewire lumen defined therethrough, the inner tubular member extending distally from a proximal port in the proximal end portion of the monolithic multilayer distal outer member through at least a portion of the balloon.

2. The balloon catheter of claim 1, wherein the second polymer comprises polyether block amide.

3. The balloon catheter of claim 2, wherein the polyether block amide has a Shore D hardness between 63D and 72D.

4. The balloon catheter of claim 1, wherein the first polymer comprises nylon.

5. The balloon catheter of claim 4, wherein the nylon is selected from the group consisting of nylon 12, nylon 11, and copolymers thereof.

6. The balloon catheter of claim 1, wherein the monolithic multilayer distal outer member further comprises at least an intermediate layer disposed between the inner layer and the outer layer.

7. The balloon catheter of claim 1, wherein the inner tubular member is coupled to the monolithic multilayer distal outer member at the proximal port.

8. The balloon catheter of claim 7, wherein the inner tubular member comprises a multilayer inner tubular member.

9. The balloon catheter of claim 8, wherein the multilayer inner tubular member comprises an inner lubricious layer and outer layer comprising polyether block amide.

10. The balloon catheter of claim 1, wherein the monolithic multilayer distal outer member is necked to the reduced diameter along an entire length thereof such that the proximal end portion has a proximate outer diameter and the distal end portion has a distal outer diameter, the proximal outer diameter being greater than the distal outer diameter.

11. The balloon catheter of claim 1, wherein the monolithic multilayer distal outer member is necked to the reduced diameter along an entire length thereof such that the monolithic multilayer distal outer member has a constant diameter along the entire length thereof.

12. The balloon catheter of claim 1, wherein the monolithic multilayer distal outer member is necked to a first reduced diameter along a first portion of the length thereof and necked to a second reduced diameter along a second portion of the length thereof such that the proximal end portion has a proximate outer diameter and the distal end portion having a distal outer diameter, the proximal outer diameter being greater than the distal outer diameter.

13. The balloon catheter of claim 12, wherein the monolithic multilayer distal outer member is necked to a third reduced diameter along a third portion of the length thereof, the third portion being proximate the proximal balloon shaft.

14. The balloon catheter of claim 1, wherein the hypotube further comprises a distal end, and an outer surface of the hypotube is roughened proximate the distal end.

15. The balloon catheter of claim 1, wherein the monolithic multilayer distal outer member has a double wall thickness of 0.009 inches to 0.012 inches.

16. A balloon catheter, comprising:
  an outer shaft including a hypotube and a monolithic multilayer distal outer member of polymer material, the outer shaft having an inflation lumen defined therethrough, the monolithic multilayer distal outer member having a proximal end portion and a distal end portion, the monolithic multilayer distal outer member having an inner layer comprising a first polymer having a tensile strength greater than 8,000 psi and an outer layer comprising a second polymer having a flexural modulus of less than 130,000 psi at room temperature, wherein a proximal end of the monolithic multilayer distal outer member is coupled to the hypotube, wherein the monolithic multilayer distal outer member is necked to a reduced diameter along an entire length thereof with the polymer material consisting essentially of polymer chains in a linear orientation, such that the proximal end portion has a proximate outer diameter and the distal end portion has a distal outer diameter, the proximal outer diameter being greater than the distal outer diameter;
  a balloon in fluid communication with the inflation lumen, the balloon having a proximal balloon shaft coupled to a distal end of the monolithic multilayer distal outer member; and
  an inner tubular member having a guidewire lumen defined therethrough, the inner tubular member extending distally from a proximal port in the proximal end portion of the monolithic multilayer distal outer member through at least a portion of the balloon.

17. The balloon catheter of claim 16, wherein the second polymer comprises polyether block amide.

18. The balloon catheter of claim 17 wherein the polyether block amide has a Shore D hardness between 63D and 72D.

19. The balloon catheter of claim 16, wherein the first polymer comprises nylon.

20. The balloon catheter of claim 19, wherein the nylon is selected from the group consisting of nylon 12, nylon 11, and copolymers thereof.

21. The balloon catheter of claim 16, wherein the monolithic multilayer distal outer member has a double wall thickness of 0.009 inches to 0.012 inches.

22. A method of making a balloon catheter, comprising:
  necking a tubular member of polymer material to form a monolithic multilayer distal outer member necked along an entire length thereof with the polymer material consisting essentially of polymer chains in a linear orientation, the monolithic multilayer distal outer member having an inner layer comprising a first polymer having a tensile strength greater than 8,000 psi and an outer layer comprising a second polymer having a flexural modulus of less than 130,000 psi at room temperature;
  providing a hypotube;
  coupling a proximal end of the monolithic multilayer distal outer member to the hypotube to form an outer shaft having an inflation lumen defined therethrough;
  providing a balloon in fluid communication with the inflation lumen, the balloon having a proximal balloon shaft;
  coupling the proximal balloon shaft to a distal end of the monolithic multilayer distal outer member; and
  providing an inner tubular member having a guidewire lumen defined therethrough, the inner tubular member extending distally from a proximal port in the monolithic multilayer distal outer member through at least a portion of the balloon.

23. The method of claim 22, wherein the monolithic multilayer distal outer member has a double wall thickness of 0.009 inches to 0.012 inches.

* * * * *